(12) United States Patent
Renuart et al.

(10) Patent No.: US 7,932,093 B2
(45) Date of Patent: Apr. 26, 2011

(54) ONE STEP OLIGOCHROMATOGRAPHIC DEVICE AND METHOD OF USE

(75) Inventors: Ismaelle Renuart, Naninne (BE); Pascal Mertens, Seilles (BE); Thierry Leclipteux, Wepion (BE)

(73) Assignee: Coris Bioconcept SPRL, Gembloux (BE)

( * ) Notice: Subject to any disclaimer, the term of this patent is extended or adjusted under 35 U.S.C. 154(b) by 327 days.

(21) Appl. No.: 10/555,154

(22) PCT Filed: Apr. 30, 2004

(86) PCT No.: PCT/BE2004/000061
§ 371 (c)(1),
(2), (4) Date: Aug. 8, 2006

(87) PCT Pub. No.: WO2004/099438
PCT Pub. Date: Nov. 18, 2004

(65) Prior Publication Data
US 2007/0202497 A1  Aug. 30, 2007

Related U.S. Application Data

(60) Provisional application No. 60/468,805, filed on May 7, 2003.

(51) Int. Cl.
*C12Q 1/68* (2006.01)
*G01N 33/558* (2006.01)
(52) U.S. Cl. .............. 436/161; 436/514; 435/6; 435/4
(58) Field of Classification Search .............. 436/161, 436/514; 435/6, 4
See application file for complete search history.

(56) References Cited

U.S. PATENT DOCUMENTS

| 4,960,691 A | 10/1990 | Gordon et al. |
| 6,037,127 A | 3/2000 | Ebersole et al. |
| 6,365,417 B1 * | 4/2002 | Fleming et al. ............... 436/514 |
| 6,485,915 B1 | 11/2002 | Keller et al. |
| 2002/0146844 A1 * | 10/2002 | Pronovost et al. ............ 436/514 |

FOREIGN PATENT DOCUMENTS

| CA | 2223705 A1 | 8/1999 |
| WO | WO 88/85534 | * 11/1988 |
| WO | 9624060 A1 | 8/1996 |
| WO | 0204667 A2 | 1/2002 |
| WO | 03033735 A2 | 4/2003 |

OTHER PUBLICATIONS

Reinhartz, et al., "A Novel Rapid Hybridization Technique: Paper Chromatography Hybridization Assay (PACHA)", Gene, 1993, pp. 221-226, Elsevier Science Publishers B.V.
Jou, et al., "Deletion Detection in the Dystrophin Gene by Multiplex Gap Ligase Chain Reaction and Immunochromatographic Strip Technology", Human Mutation, 1995, Wiley-Liss, Inc. 1995, 8 pgs.
Mertens, et al., "Detection of Toxoplasma Gondii byOligochromatography of Nested-PCR Ampli-Cons", 1 pg., Coris BioConcept, Belgium.
Fong, et al., "Rapid Solid-Phase Immunoassay for Detection of Methicillin-Resistant *Staphylococcus aureus* Using Cycling Probe Technology", Journal of Clinical Microbiology, Jul. 2000, pp. 2525-2529.

* cited by examiner

*Primary Examiner* — Walter D Griffin
*Assistant Examiner* — Christine T Mui
(74) *Attorney, Agent, or Firm* — Fitch, Even, Tabin & Flannery

(57) ABSTRACT

The present invention relates to methods and devices for detecting one or more analytes in a biological sample, preferably a clean liquid sample. This invention in particular relates to improved rapid tests such as "dipsticks", "lateral flow" devices and "flow-through" devices. The invention in particular relates to oligochromatographic devices that make use of a peptide- or hapten-coupled oligonucleotide and a reagent specifically recognizing the hapten or peptide and a conjugated probe that hybridizes specifically to a target sequence. It allows to detect specifically the presence of a polynucleotides directly or after molecular amplification steps with the use of a specific genuine internal control and a chromatographic control.

34 Claims, 2 Drawing Sheets

SEQUENCE LISTING

<160> NUMBER OF SEQ ID NOS: 15

<210> SEQ ID NO 1
<211> LENGTH: 20
<212> TYPE: DNA
<213> ORGANISM: Toxoplasma gondii
<220> FEATURE:
<223> OTHER INFORMATION: N-STX1-F2 oligonucleotide probe -continued

```
<400> SEQUENCE: 1
cttcttatct ggatttaatg                                                20

<210> SEQ ID NO 2
<211> LENGTH: 20
<212> TYPE: DNA
<213> ORGANISM: Toxoplasma gondii
<220> FEATURE:
<223> OTHER INFORMATION: N-STX2-F3 oligonucleotide probe

<400> SEQUENCE: 2
tctgtgtata cgatgacgcc                                                20

<210> SEQ ID NO 3
<211> LENGTH: 23
<212> TYPE: DNA
<213> ORGANISM: Toxoplasma gondii
<220> FEATURE:
<223> OTHER INFORMATION: stx1-F forward primer

<400> SEQUENCE: 3
ataaatcgcc attcgttgac tac                                            23

<210> SEQ ID NO 4
<211> LENGTH: 21
<212> TYPE: DNA
<213> ORGANISM: Toxoplasma gondii
<220> FEATURE:
<223> OTHER INFORMATION: stx1-R-biot reverse primer, biotinylated in
      the 5' position

<400> SEQUENCE: 4
agaacgccca ctgagatcat c                                              21

<210> SEQ ID NO 5
<211> LENGTH: 21
<212> TYPE: DNA
<213> ORGANISM: Toxoplasma gondii
<220> FEATURE:
<223> OTHER INFORMATION: stx2-F forward primer

<400> SEQUENCE: 5
ggcactgtct gaaactgctc c                                              21

<210> SEQ ID NO 6
<211> LENGTH: 22
<212> TYPE: DNA
<213> ORGANISM: Toxoplasma gondii
<220> FEATURE:
<223> OTHER INFORMATION: stx2-R-DIG reverse primer, digoxigenated in
      the 5' position

<400> SEQUENCE: 6
tcgccagtta tctgacattc tg                                             22

<210> SEQ ID NO 7
<211> LENGTH: 20
<212> TYPE: DNA
<213> ORGANISM: Artificial Sequence
<220> FEATURE:
<223> OTHER INFORMATION: oligonucleotide probe for T. gondi target
      gene

<400> SEQUENCE: 7
ccctctgctg gcgaaaagtg                                                20
```

```
<210> SEQ ID NO 8
<211> LENGTH: 23
<212> TYPE: DNA
<213> ORGANISM: Artificial Sequence
<220> FEATURE:
<223> OTHER INFORMATION: oligonucleotide for internal control

<400> SEQUENCE: 8
agggtctact actgggttac ctg                                              23

<210> SEQ ID NO 9
<211> LENGTH: 15
<212> TYPE: DNA
<213> ORGANISM: Artificial Sequence
<220> FEATURE:
<223> OTHER INFORMATION: migration control oligonucleotide

<400> SEQUENCE: 9
caggtaaccc agtag                                                       15

<210> SEQ ID NO 10
<211> LENGTH: 89
<212> TYPE: DNA
<213> ORGANISM: Artificial Sequence
<220> FEATURE:
<223> OTHER INFORMATION: Toxo internal control template

<400> SEQUENCE: 10
ggttgcagtc actgacgagc tcagggtcta ctgggttacc tgaaagtcat gagtatctgt     60
gcaactttgg tgtattcgca gattggtcg                                        89

<210> SEQ ID NO 11
<211> LENGTH: 20
<212> TYPE: DNA
<213> ORGANISM: Artificial Sequence
<220> FEATURE:
<223> OTHER INFORMATION: T. Gondii B1 Gene forward primer

<400> SEQUENCE: 11
ggttgcagtc actgacgagc                                                  20

<210> SEQ ID NO 12
<211> LENGTH: 21
<212> TYPE: DNA
<213> ORGANISM: Artificial Sequence
<220> FEATURE:
<223> OTHER INFORMATION: T. Gondii B1 Gene reverse primer,
      biotin-labelled

<400> SEQUENCE: 12
cgaccaatct gcgaatacac c                                                21

<210> SEQ ID NO 13
<211> LENGTH: 91
<212> TYPE: DNA
<213> ORGANISM: Artificial Sequence
<220> FEATURE:
<223> OTHER INFORMATION: T7 RNA polymerase promoter internal control
      template

<400> SEQUENCE: 13
taatacgact cactataggg aggcacccgc gaagaagcta ttctttaggg tctactgggt     60
tacctgccgg atgtagaggg ctgtcatgca a                                    91

<210> SEQ ID NO 14
<211> LENGTH: 22
```

```
<212> TYPE: DNA
<213> ORGANISM: Artificial Sequence
<220> FEATURE:
<223> OTHER INFORMATION: SARS-CoV target gene reverse primer, biotin
      labelled

<400> SEQUENCE: 14
ttgcatgaca gccctctaca tc                                                22

<210> SEQ ID NO 15
<211> LENGTH: 20
<212> TYPE: DNA
<213> ORGANISM: Artificial Sequence
<220> FEATURE:
<223> OTHER INFORMATION: Sars-CoV target gene forward primer

<400> SEQUENCE: 15
cacccgcgaa gaagctattc                                                   20
```

ONE STEP OLIGOCHROMATOGRAPHIC DEVICE AND METHOD OF USE

FIELD OF THE INVENTION

Figure 1:
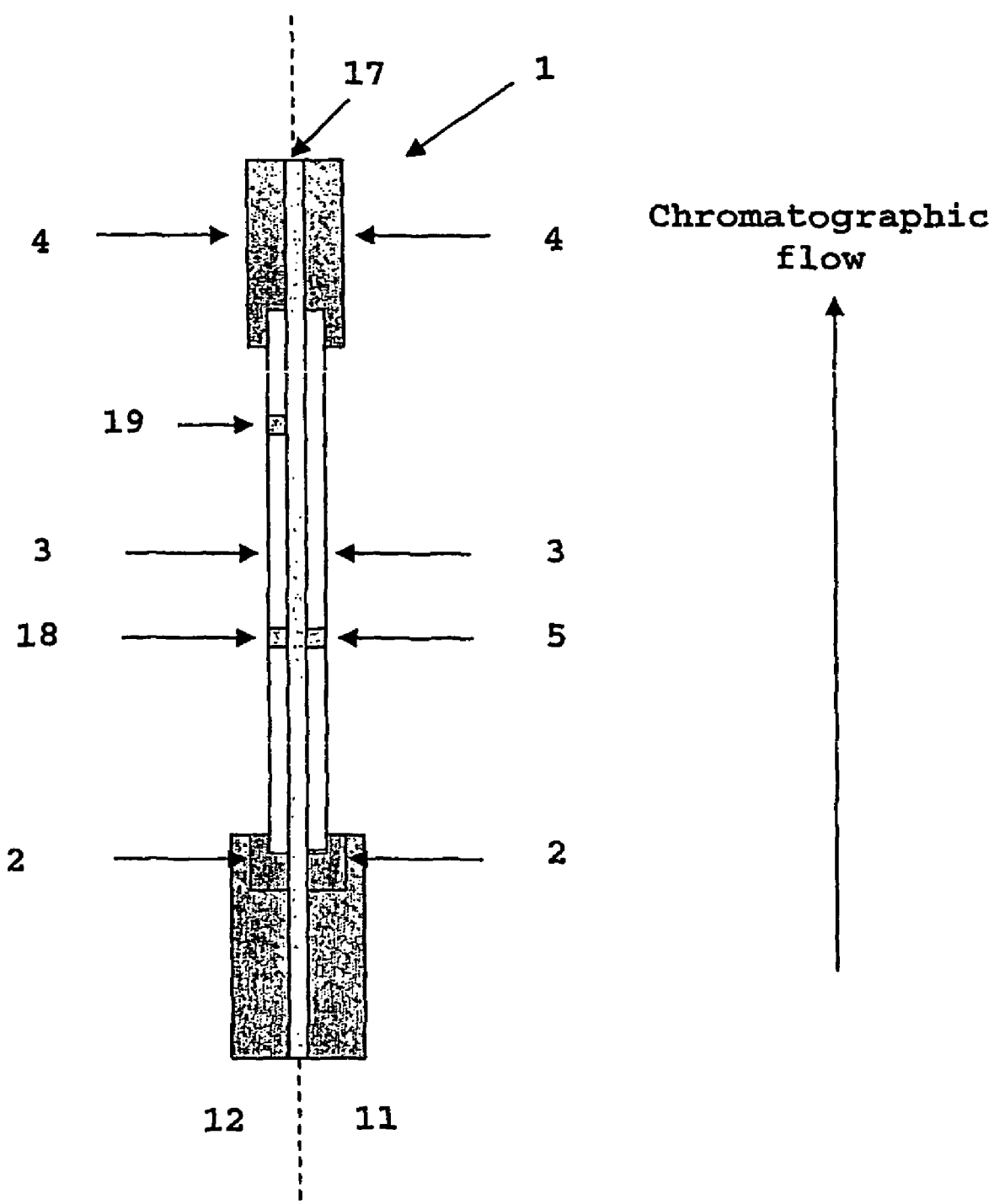

This invention relates to methods and devices for detecting analytes in biological samples. This invention relates to rapid tests and typical rapid tests include "dipstick", "lateral flow" devices and "flow-through" devices.

STATE OF THE ART

Several approaches have been developed for detection of analytes in a biological sample for routine diagnostics in laboratories via immunochromatography.

EP 0 088 636, EP 0 186 799, EP 0 284 232 and WO 88/08534 disclose sheet-like chromatographic devices comprising at least a first and a second region. Prior art devices disclosed in these documents comprise:
- a first region containing porous active material to allow liquid to move to the sensitized region coated with specific reagents. This first region, referred to as sample pad, comprises a detection reagent dried on it or impregnated into it. It may further contain an application region and/or an absorption (sub)region. Sample pad region is generally referred to as the application region;
- a second region, also referred to as the detection region, made of porous active material on which specific reagents are adsorbed. Some of these reagents sprayed onto a line of the second region of the device are directly or indirectly specific for the analyte to be detected and should react with the sample analyte-labeling reagent complex while other non-specific reagents eventually sprayed onto a further line of the second region are dedicated to react with the excess of the detection reagent. This second region, preferably made out of nitrocellulose, may also contain a control line, preferably behind the detection region; and
- possibly also a third region made of porous material dedicated to absorb excess of liquid coming through the first and second regions. This region is generally referred to as the adsorbent or absorbent region.

Several other detection techniques known in the art relate to detection of molecules produced after a preliminary process like molecular or genetic amplification of an analyte.

AIMS OF THE INVENTION

The present invention aims to provide a new and inventive technique for the detection of polynucleotide molecules possibly obtained after molecular amplification steps.

It is a further aim of the invention to provide devices which are easy to handle and which allow rapid but accurate detection and/or diagnosis.

DEFINITIONS

Primer: Analyte specific oligonucleotide (used for amplification, labelled to react with the capture reagent)

Conjugate: Analyte specific probe coupled with a direct particulate label

Capture reagent: reagent that will react specifically with the labelled analyte specific oligonucleotide Absorbent pad: first region or sample pad Conjugate pad: region that contains the dried conjugate

SUMMARY OF THE INVENTION

The present invention relates to a sheet-like chromatographic device, in particular dipsticks, flow-through and lateral flow devices, having
- an application region (optionally with conjugation pad),
- a detection region (possibly with control portion (e.g. control lines)), and
- optionally an absorbent region. The detection region comprises at least one capture reagent specifically recognizing a hapten or peptide conjugated with or coupled to an analyte-specific oligonucleotide; and the application region comprises at least one specific labelled conjugate (with direct or indirect label) preferably an oligonucleotide (DNA, RNA, PNA, LNA) that hybridizes specifically with the analyte and generally designated as a probe. In case of a positive reaction, i.e. in case a complex is formed between said specific (capture) reagent and said hapten- or peptide-coupled specific analyte hybridized with said specific conjugate, a signal is generated. This signal is also referred to as the specific signal. The analyte-specific oligonucleotide is one of the primers used for the molecular amplification of the analyte(s).

In a particular embodiment of the invention, the control line is made of an oligonucleotide sequence that hybridizes with the specific conjugate probe The capture reagent may be a polyclonal or monoclonal antibody or an hypervariable antibody fragment or a molecule that interacts specifically with the hapten or peptide or any molecule conjugated or coupled to the analyte specific oligonucleotide. The detection label preferably is a direct particulate label, preferably selected from the group consisting of conjugated metallic colloids, conjugated latex particles and microparticles having a particular color.

Preferably, the sheet-like chromatographic device is composed of polymeric substances laminated on a rigid polymer. In a preferred embodiment, the application region comprises a membrane made of glass fibers with a conjugate pad made of polyester, the detection region comprises a membrane made of nitrocellulose and the adsorbent region comprises a membrane made of cellulose. According to another embodiment, the application region and conjugate pad are made of the same material.

The present invention further relates to detection methods that make use of one of the above-described devices, also referred to as the oligochromatographic devices, which can be used to check the presence of target oligonucleotide sequences preferably after amplification. Detection can be performed via the naked eye and/or automatically with the aid of a strip-reader and specific software programs for the detection and/or quantification of analytes or amplicons.

The present invention is further illustrated by the following non limiting examples and embodiments, in reference to the enclosed figures.

SHORT DESCRIPTION OF THE INVENTION

The FIG. 1 represents a positive test obtained with the detection device of the invention.

Figure 2A:
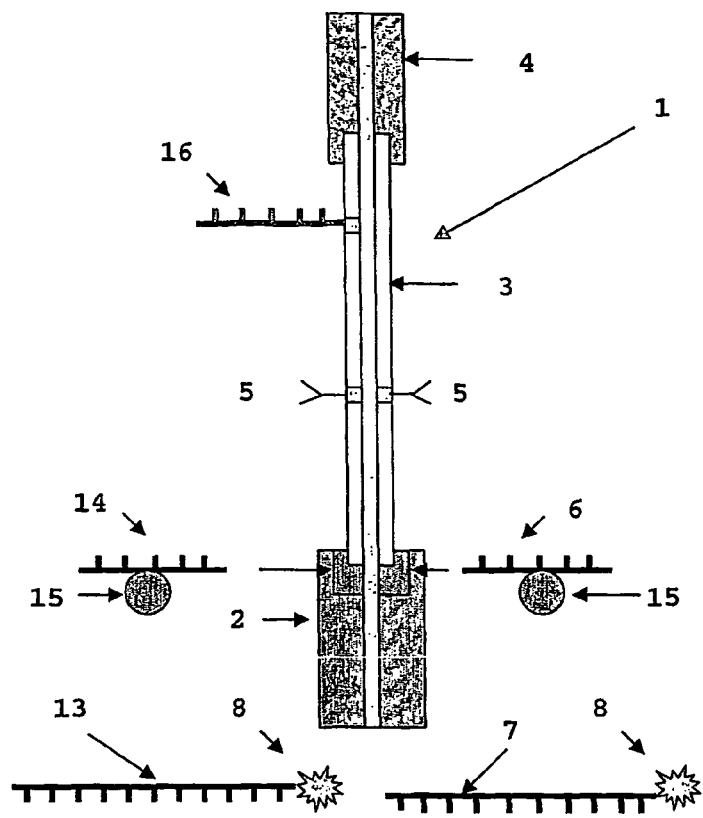
Figure 2B:
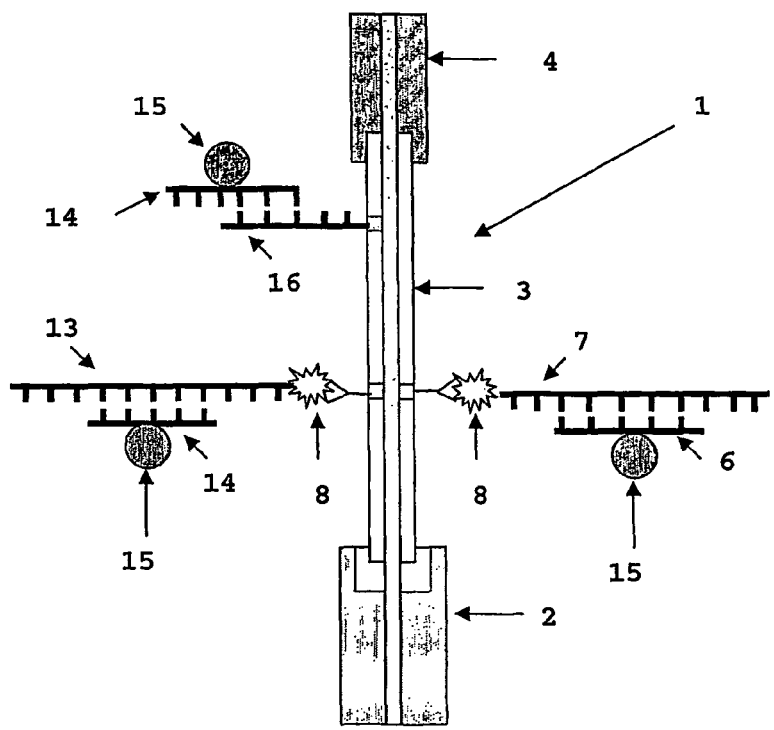

The FIGS. 2a and 2b represent the various detection steps of the method of the invention.

DETAILED DESCRIPTION OF THE INVENTION

The present invention relates in particular to improved analyte detection devices (1) either chromatographic devices such as improved lateral flow, or dipstick devices or either flow-through systems and their use in the detection of analytes possibly present in a sample such as a clean liquid sample. Preferred devices comprise an application region (2), a detection region (3) and possibly an adsorption region (4) as known in the art. The detection region (3) may contain one or more defined portions, preferably lines, each dedicated to the detection of one particular analyte or group of analytes. There may be included a control region, possibly containing several portions (lines). The devices of the invention may be one-piece sheet-like devices or may be comprised of several parts in capillary contact with each other. Flow-through devices should be considered also as a tool for the present invention.

The devices according to the invention are composed of porous polymeric substances that preferably are laminated on a rigid or semi-rigid polymer to provide mechanical strength which makes the device easy to handle. The porosity of the polymeric substances should be such that capillary migration of a fluid and its components from the bottom to the top of the stick, moving along rehydrated conjugate, is possible without any hindrance. These characteristics are allowed by the hydrophilic properties of these polymers. Examples of suitable polymers are cellulose, nitrocellulose, cellulose acetate, glass fibers, nylon, acrylic copolymer/nylon, polyethersulfone and polyester.

A specific labelled reagent (6), which is specific for the analyte, serves to detect and/or quantify analytes possibly present in a clean liquid sample. The specific labelled reagent (6) will form a complex with the analyte, which complex is then captured by a specific capture reagent (5). This capture reagent (5) may be a polyclonal or monoclonal antibody or any hypervariable antibody fragment known in the art or any other molecule that could bind specifically to a complementary molecule such as haptens, peptides or proteins (8) that could specifically react with the labeled analyte. These reagents may be produced via genetic engineering.

Various detection systems are known in the art. Colored or visible (direct) particulate labels known in the art include particles (15) made of latex polymers, metallic colloids such as gold, carbon, liposomes, . . . which can be conjugated to the binding reagent (6) that normally reacts with the analyte to be detected. With both systems, quantification and/or semi-quantification are possible.

The present invention relates to a method for rapid and specific detection of presence of target nucleic acid products (7) preferably after molecular amplification of an analyte. Any molecular amplification technique, including but not limited to PCR, RT-PCR, LCR or NASBA, may be used to generate an amplified product (7). Nucleic acid products include among others single-stranded, double-stranded or partly double-stranded DNA, RNA molecules or the like. The backbones of the molecules may be modified and/or may include nucleotide or nucleoside analogues.

In a preferred embodiment of the invention, the specific probe conjugate comprises a visible (direct) label (15) conjugated to a polynucleotide sequence (DNA, RNA, PNA, LNA) (6) that hybridizes specifically with the specific target sequence (7). With specific hybridization is meant that the conjugated polynucleotide sequence will hybridize under particular conditions (well known by the person skilled in the art) with the analyte which would be present in the liquid, and not with other nucleic acid sequences. It is thereby possible to detect a particular analyte within a mixture of compounds, possibly containing several other analytes. The complex formed between the oligonucleotide sequence of interest (7) and the specific probe conjugate will move into the membrane of the second region (3) (preferably nitrocellulose) and reaches the capture reagent (5) (polyclonal or monoclonal antibody or any hypervariable antibody fragment known in the art or any molecule that could be haptens, peptides or proteins that could specifically react with the labeled analyte which are coated thereon. The reaction between the complex (6-15) and its specific reagent (5) coated onto the membrane will be visualized, since the particles (15) will accumulate and generate a visible signal. This signal allows the user to evaluate that the polymerization process performs correctly and specifically if an amplification process was carried out.

The current invention thus in particular relates to a device that allows the user to check within minutes whether a specific molecular amplification has been performed or not. The device further may allow quantification or semi-quantification of the amount of amplicons produced.

Below, more details are provided with respect to general aspects and preferred compositions and build-up of the particular oligochromatographic devices according to the present invention.

The devices according to the invention comprise application (2), detection (3) and absorbent (4) regions and optionally a control region (internal control) with one or more control lines.

In a preferred embodiment, the membrane of the application region (2) is made of glass fibers with a conjugate pad made of polyester, the membrane of the detection region is made of nitrocellulose e.g. from Advanced Microdevices Pvt, Ltd. Membranes from another supplier (e.g. Schleicher & Schuell, Pall or Millipore) can also be used. The membrane of the absorbent region is preferably made of cellulose. In particular embodiments, application region and conjugate pad can be made of the same material. The conjugate can, however, also be adsorbed directly onto the application region.

In another preferred embodiment, the application region (2) is made of a rigid polymer to which a covering absorbent pad made of glass fibers is adhered, absorbing and conducting the sample liquid to the detection region. The glass fibers may further cover a conjugate pad made of polyester that contains the conjugate under a dry form. Also this pad should have such characteristics that the conjugate will be easily hydrated by the sample liquid to allow a complete removal of the hydrated conjugate and specific reaction of the conjugate reagents with their specific analyte.

The conjugate pad can be fully or partially covered by the sample pad. Both sample pad and conjugate pad could be made of the same matter or material. In this case, the conjugate could be directly sprayed onto the polymer that is also used to absorb the sample liquid.

The conjugate pad is impregnated with particles that are coated with some compounds that could include proteins, peptides, haptens, polysaccharides, lipopolysaccharides, nucleic acids, PNA or LNA or other polymeric molecules that can specifically hybridize with DNA and/or RNA. These compounds will react somewhere specifically with analytes that could be present into the samples to be analyzed. Examples of particles include colloidal gold particles, colloidal sulphur particles, colloidal selenium particles, colloidal barium sulfate particles, colloidal iron sulfate particles, metal iodate particles, silver halide particles, silica particles, colloidal metal (hydrous) oxide particles, colloidal metal sulfide particles, colloidal lead selenide particles, colloidal cadmium selenide particles, colloidal metal phosphate particles, colloidal metal ferrite particles, any of the above-mentioned colloidal particles coated with organic or inorganic layers, protein or peptide molecules, liposomes, colored microparticles or organic polymer latex particles.

In a preferred embodiment, particles are colloidal gold particles with a diameter of about 5 to about 40 nm. Preferably, particles with a diameter of about 20 nm or about 40 nm are used. Polystyrene latex beads that have been activated with several chemical functions such as carboxyl one, amine one, hydroxyl one and sulfhydril one could be used. In one preferred embodiment, carboxylated amino or sulphydryl (without limitations) latex particles are used.

Alternatively, colored microparticles may be used. In order to perform multicolor detection of multiplex PCR or any other different nucleotidic sequences, oligonucleotide probes can be coupled to differently colored microparticles. Each oligonucleotide probe, specific for one particular target nucleic acid, will then be associated with one particular color (e.g. red for analyte A and blue for analyte B).

Several cross-linking reagents are available for specific coupling of functional groups, present on microparticles, to a modified oligonucleotide. One method is the covalent coupling of an amino-modified oligonucleotide to COOH-modified microparticles which can be purchased from several manufacturers and exist in various colors and diameters. Amino-modified oligonucleotides can be coupled to these COOH-modified microparticles through the use of specific coupling agents like for example carbodiimide (with or without hydroxysuccinimide ester). The coupling of molecules with for instance a carboxyl, amino or sulfhydryl group (naturally present or chemically synthesized) through the use of homo- or hetero-bifunctional cross-linking reagents are well described in the art.

Particles to be used in the oligochromatographic devices of the invention are coated with compounds that either bind specifically with the analyte to be detected, or that bind specifically with compounds that will react with a reagent that has been coated onto the detection region. In a preferred embodiment, the analyte to be detected consists of nucleic acid amplified sequences.

The use of labelled oligonucleotides (e.g. the haptens biotin or digoxigenin labelled oligonucleotides) as primers to allow the detection of amplified products is also well known in the art. Also peptide-labelled oligonucleotides are described. In the present invention, peptide- or hapten-labelled oligonucleotides are used as a primer in a nucleic acid amplification reaction or in molecular amplification steps, and an reagent directed against said hapten or peptide is then used to detect amplicon formation, as indication for the presence of an analyte in a test sample.

It is known in the art how to generate specific immunoreagents against an antigenic peptide or a hapten. Monoclonal antibodies directed against haptens, such as digoxigenin and for instance biotin, are readily available in the art.

Coating preferably is performed by diluting the reagent in an appropriate buffer and by distributing it onto the membrane, preferably nitrocellulose, with a contact system (e.g. IsoFlow from Imagen Technology). Speed distribution could vary from about 50 mm to about 10 mm/sec but is preferably fixed to about 40 mm/sec or even better at about 30 mm/sec. Volume of material distributed varies from about 0.5 to about 3 µl/cm, preferably from about 0.7 to about 2 µl/cm and more precisely from about 1 to about 2 µl/cm.

Reagent concentration varies from about 0.1 to about 5 mg/ml and preferably is about 1 mg/ml. In a preferred embodiment of the invention, the buffer used for this coating consisted of a saline solution (NaCl) buffered with phosphate at about pH 7.2.

In an embodiment of the invention, the device includes an absorbent region that aspirates solution that has been transported by capillary action to the end of the nitrocellulose. Examples of substances include cellulose and glass fibers. Cellulose (MDI) or borosilicate glass fiber (Schleicher & Schuell) has been preferably used.

In a particular embodiment according to this invention, gold conjugate is impregnated into a solid inert membrane that could be polyester or nylon. Polyester is preferred. The polyester membranes used here have a size of 27×260 mm and are from Advanced Microdevices Pvt, Ltd (India). The membranes are impregnated with the gold conjugate after a dilution step in a specific buffer to provide an optimal rehydratation with the liquid sample when the test is running. AccuFlow G membranes from Schleicher & Schuell are also useful for this purpose and give the advantage that the conjugate is directly sprayed onto the sample matrix.

When using the polyester membranes from Advanced Microdevices Pvt, the membranes are impregnated by dipping into an appropriate vial with a finite volume that is about 1.6 ml but that could be reduced to 1.3 ml depending on the impregnation system used. Membranes are let to dry at room temperature overnight. They are then dried in an oven at about 55° C. for about 20 minutes. After drying, those membranes are stored in specific boxes with desiccants under a maximum of 10% of relative humidity. Membranes are cut into about 5 mm width pieces and stuck onto the adhesive part of the laminates. An absorbent paper made of glass fibers, or any other absorbent matter, is then stuck onto the adhesive part of the strip provide it covers tightly the polyester membrane to allow the liquid to rehydrate the conjugate and let him react with the antigens present in the sample.

When AccuFlow G membranes are used, the conjugate is sprayed with the IsoFlow Atomizing Nozzle system from Imagen Technology. In this case the conjugate is sprayed at a speed of 50 mm/sec for quantities sprayed ranging from 0.8 µl/mm to 1.67 µl/mm with a pressure ranging from 1 to 20 psi.

In a further particular embodiment according to invention, oligonucleotides are coupled to colloidal gold particles. Size of gold particles could vary from about 5 to about 60 nm, but preferably from about 20 to about 40 nm. In this description, particles of about 20 nm have been used. The oligonucleotide conjugate is then processed to be dried either onto a polyester conjugate pad or directly onto the sample material as described hereabove.

EXAMPLES

Example 1

Detection of *Toxoplasma gondii*

Preparation of Colloidal Gold Particles

Colloidal gold particles of about 20 nm were prepared by reduction of tetrachloroauric acid with sodium citrate. Two hundred ml of ultrapure water containing about 60 mg of $HAuCl_4.3H_2O$ were heated to boiling and about 5 ml of a 4% dihydrate sodium citrate solution are added. Boiling was continued for a few minutes, until a dark red solution was obtained. The solution was let to equilibrate at room temperature before use. The $OD_{520nm}$ was measured to evaluate particles concentration in the solution.

Coupling of Oligonucleotides to Colloidal Gold Particles

Coupling oligonucleotide to colloidal gold particles is well known in the art. Thiol-labelled oligonucleotides are reacted with colloidal gold particles. In the present case, 5'-amino-modified oligonucleotides were modified by N-succinimidyl S-acetylpropionate (SATP) to obtain oligonucleotides with protected sulfhydryl (thiol) group. This protected sulfhydryl group was further deprotected. These reactions were performed essentially as described by the SATP manufacturer (Pierce, Rockford, Ill.). Two oligonucleotides were used as probes in the Toxoplasmosis oligochromatographic device: one specific for the *T. gondii* target gene (5' CCCTCTGCTG-GCGAAAAGTG 3'), and one specific for the internal control (5' AGGGTCTACTACTGGGTTACCTG 3').

Briefly, 5'-amino-modified oligonucleotides in 50 mM Sodium Phosphate, 1 mM EDTA buffer, pH 7.5 are mixed with 10-fold molar excess of SATP and reaction proceeds for 30 minutes at room temperature. Excess SATP is removed by desalting on an exclusion chromatography column (NAP-5, Amersham Biosciences), following instructions of the manufacturer. SATP-labelled oligonucleotide is eluted in a 50 mM Sodium Phosphate, 1 mM EDTA buffer, pH 7.5. SATP-labelled oligonucleotides can be stored at −20° C. until needed. Deprotection was subsequently performed by adding hydroxylamine (0.5M final concentration) for 2 hours at room temperature. Excess hydroxylamine was removed by desalting. Resulting thiol-labelled oligonucleotides are mixed with colloidal gold particles (at 4.2 $OD_{520}$/ml, final concentration) for 24 hours. Sodium Phosphate pH7.0 at 10 mM final concentration and NaCl at 0.1M final concentration are then added. The mix is incubated for another 24 hours. NaCl at 0.2M final concentration is then added and the mix is incubated for 16 hours. Excess oligonucleotide is removed by centrifugation and two successive washings of the pelleted gold particles with 10 mM Sodium Phosphate, 0.3M NaCl buffer, pH 7.0 were performed. Oligonucleotide-gold conjugates are finally stored in the same buffer.

The Oligochromatographic Device

The oligochromatographic device (1) that was used in the present example consists of a backing solid support (17) such as a plastic element with thereupon an application region (2) made preferably of polyester conjugate pad from MDI, a detection region (3) preferably made of nitrocellulose and an adsorption region (4) preferably made of cellulose. These materials are advantageously present on both sides (11, 12) of the backing plastic (17). One side, called the test side (11), is dedicated to the detection of the (*T. gondii*) target polynucleotide. The other side, called the control side (12), is dedicated to the detection of an amplification internal control and also has migration control (16 elements).

On the test side (11), the nitrocellulose membrane was preferably sensitized with neutralite avidine. The (*T. gondii*) specific oligonucleotidic probe conjugate is impregnated in the polyester membrane (MDI) of the application region (2) of this test side (11).

On the control side (12), the nitrocellulose membrane has two lines (19, 18). The lower, internal control amplification test line (18), is preferably sensitized with neutralite avidine. Preferably, the upper, migration test line (19), is sensitized with the migration control oligonucleotide which sequence (5' CAGGTAACCCAGTAG 3') is anti-parallel to that of the internal control probe. For this coating, the 5'-biotinylated migration control oligonucleotide is mixed with neutralite-avidine used as a carrier protein. The internal control specific oligonucleotidic probe conjugate (14, 15) is impregnated in the polyester membrane (MDI) of the application region (2) of this control side (12) (FIG. 2b).

Amplification of the Internal Control

The internal control is designed as to show if a negative *T. gondii* test result is a true negative, i.e. that the negative result is not due to an amplification inhibitory substance possibly present in the tested sample. This internal control is a template that is added to the reaction mix before the amplification, and should be amplified at least in the absence of *T. gondii* target gene, unless an inhibitory substance is present in the sample.

The internal control template is an oligonucleotide that was designed with the following criteria:
- (almost) same length as the target amplicon
- (almost) same G/C content as the target amplicon
- amplified with the same oligonucleotidic primers as the target amplicon
- in the internal part of this internal control template, the sequence of the *T. gondii* target gene probe is replaced by the sequence of the internal control probe. In that way, the *T. gondii* specific probe does not hybridize to the internal control amplicon, and the internal control probe does not hybridize to the *T. gondii* target gene amplicon. Following these criteria, the sequence of the Toxo internal control template is: 5' GGTTGCAGTCACTGAC-GAGCTCAGGGTCTACTGGGTTACCTGAAAGTC ATGAGTATCTGTGCAACTTTGTATTCGCAGATT GGTCG 3' (sequence of the internal control probe underlined).

The quantity of the Toxo internal control template to be added to the amplification mix has been determined as to allow amplification of this internal control in all cases (24/24) in the absence of sample. The inventors also showed that in the presence of SDS 0.01% used as a moderate inhibitor, the internal control was not detected anymore after PCR.

DNA Extraction

Extraction of DNA from samples containing *T. gondii* was realized using the "EXTRAcell DNA extraction" kit (Bioline, Torino, Italy) following manufacturer's instructions. DNA can be extracted by any other method, either commercially available or described in the scientific literature. Extracted DNA is used directly after extraction or kept at −20° C. until use.

Amplification of Target DNA

*T. gondii* B1 gene amplification was performed by PCR with a biotin-labelled reverse primer.

Amplification mix (45 µl per reaction) contains the following materials (final concentrations are indicated as for the mix including the 5 µl sample):
- each of the four dNTPs (DATP, dCTP, dGTP and dTTP) at 0.1 mM final concentration (for each)
- PCR buffer including MgCl2, 1× final concentration (Sigma)
- Taq polymerase, 2 Unit (Sigma)
- Internal control oligonucleotide template, 1.67 10−22 mole.

The forward primer (5' GGTTGCAGTCACTGACGAGC 3') was used at 0.1 µM final concentration and the biotin-labelled reverse primer (5' CGACCAATCTGCGAATA-CACC 3') at 0.4 µM final concentration.

Up to 5 µl of extracted DNA can be used to perform the amplification. If less than 5 µl is used, molecular biology grade water is added to reach a total reaction volume of 50 µl.

Amplification is performed with the following thermic cycles:
- 5 minutes at 94° C.
- 45 cycles (20 seconds at 94° C., 20 seconds at 55° C., 30 seconds at 72° C.)
- 1 minutes at 72° C.
- 30 seconds at 94° C.

Amplified products are the stored at 4° C. until further use.

*T. gondii* Detection

Forty to up to fifty µL of the amplified product is pipetted in a tube containing 3 times this volume of oligochromatographic buffer pre-equilibrated at 55° C. The oligochromatographic stick is put in the tube immediately, and the assay tube is closed. The chromatography proceeds for up to 10 minutes (the tube being maintained at 55° C. in a heating-block or other device). The amplified product migrates in the stick and the dried gold-conjugated oligonucleotide probes are rehydrated. On the test side of the stick, the probe hybridizes specifically with the *T. gondii* target gene amplified product. The complex then migrates on the nitrocellulose and the complex is captured by the immobilized neutralite avidin through the biotin label present in the amplified product (the reverse oligonucleotide in the amplification being biotin-labelled). The capture of the complex gives rise to a positive signal, i.e. a line where the colloidal gold particles accumulate to give a pink to purple color. On the control side of the stick, the internal probe conjugate hybridizes specifically with the internal control amplified product. The complex then migrates on the nitrocellulose and the complex is captured by the immobilized neutralite avidin (the internal control being amplified with the same biotin-labelled reverse oligonucleotide). The capture of the complex gives rise to a positive signal. The remaining non-reacted internal control probe conjugate migrates further to the migration control line where it hybridizes with the immobilized migration control oligonucleotide, giving rise to a positive signal.

Example 2

Detection of Toxins STX1 & STX2 of *E. coli* O157:H7

DNA Extraction

Extraction of DNA from samples of cultures of *E. coli* with or without stx1 and stx2 genes was realized using the "EXTRAcell DNA extraction" kit (Bioline, Torino, Italy) following manufacturer's instructions. DNA can be extracted by any other method, either commercially available or described in the scientific literature. Extracted DNA is used directly after extraction or kept at −20° C. until use. Tested *E. coli* strains included ATCC strains numbers 35150, 43890 and 25922 (incorporated herein by reference) as positive and negative controls, respectively.

stx1-stx2 Oligochromatographic Stick

An oligochromatographic (dip)stick for the specific detection of the amplified stx1 and stx2 genes was build up conform to the test side of the oligochromatographic stick for the specific detection of the amplified *T. gondii* B1 gene, except that two colloidal gold-labelled oligonucleotide probes specific for the stx1 and stx2 amplified products were mixed and dried in the conjugate pad. The sequences of the oligonucleotide probes are the following:

```
N-STX1-F2: 5'-CTTCTTATCTGGATTTAATG-3' (SEQ ID NO:1)
for the detection of amplified stx1 gene N-STX2-F3: 5'-TCTGTGTATACGATGACGCC-3' (SEQ ID NO:2)
for the detection of amplified stx2 gene
```

Both oligonucleotide contain an amine in the 5' position. Modification of this amine into a thiol group for coupling to colloidal gold particles was realized as described above.

Amplification of stx1 and stx2 Genes

In order to detect both stx1 and stx2 *E. coli* genes encoding shiga-like toxin I and II, respectively, internal sequences of these genes have been amplified using the oligonucleotide primers described by Paton and Paton (J. Clin. Microbiol., February 1998, vol. 36 (2): 598-602). Forward and reverse primers for the amplification of stx1 are stx1-F (5'-ATAAATCGCCATTCGTTGACTAC-3', SEQ ID NO:3) and stx1-R-biot (5'-AGAACGCCCACTGAGATCATC-3', SEQ ID NO:4), respectively.

Primer stx1-R-biot is biotinylated in the 5' position. Forward and reverse primers for the amplification of stx2 are stx2-F (5'-GGCACTGTCTGAAACTGCTCC-3', SEQ ID NO:5) and stx2-R-DIG (5'-TCGCCAGTTATCTGACATTCTG-3', SEQ ID NO:6), respectively. Primer stx2-R-DIG contains a Digoxigenin group in the 5' position.

Amplification mix (50 μl per reaction) contains the following materials:

each of the four dNTPs (DATP, dCTP, dGTP and dTTP) at 0.3 mM final concentration
PCR buffer, 1× final concentration (Sigma)
Taq polymerase, 1 Unit (Sigma)

Each of the forward primers was used at 0.1 μM final concentration and each of the reverse primers at 0.5 μM final concentration.

Up to 5 μl of extracted DNA can be used to perform the amplification.

Amplification is performed with the following thermic cycles:

5 minutes at 94° C.
35 cycles (30 seconds at 94° C., 30 seconds at 55° C., 45 seconds at 72° C.)
2 minutes at 72° C.
30 seconds at 94° C.
storage at 4° C. until use Oligochromatographic Testing for stx1 and stx2 Genes The oligochromatographic test for the detection of stx1 and/or stx2 amplified gene(s) is performed similarly as for the detection of amplified *T. gondii* B1 gene except that the specific stx1-stx2 stick is used. In this stick, two "receptors" are coated on the nitrocellulose: one antibody specifically binds digoxigenin and will capture all digoxigenin-labelled molecules, comprising stx2 amplified gene in complex with stx2 colloidal gold-labelled probe. The second receptor is neutralite-avidin and specifically binds biotin and will capture all biotin-labelled molecules, comprising stx1 amplified gene in complex with stx1 colloidal gold-labelled probe.

Fifty μl of the amplified product is pipetted in a tube containing the same volume (50 μl) of oligochromatographic buffer heated at 55° C. The stx1-stx2 immunochromatographic stick is put in the tube immediately, and the chromatography proceeds for up to 10 minutes (the tube being maintained at 55° C. in a heating-block or other device). The amplified product migrates in the stick and the two dried gold-conjugated oligonucleotide probes are rehydrated and the probes hybridize specifically with the amplified products. The complexes then migrate on the nitrocellulose and the complexes are captured specifically by the immobilized anti-hapten antibodies through the hapten labels. The capture of the stx1 complex gives rise to a positive signal on the line coated with neutralite-avidin, i.e. a band where the colloidal gold particles accumulate to give a pink to purple line. The capture of the stx2 complex gives rise to a positive signal on the line coated with anti-digoxin, i.e. a band where the colloidal gold particles accumulate to give a pink to purple line.

All results obtained by the oligochromatographic method were in accordance with results obtained by analysis of the PCR amplicons on agarose gel and with the known status of the reference and other tested strains.

The second example shows the detection of the SARS-CoV RNA

Example 3

Detection of SARS-CoV Virus

Preparation of Colloidal Gold Particles

Colloidal gold particles of about 20 nm were prepared as described above.

Coupling of Oligonucleotides to Colloidal Gold Particles

Oligonucleotides used as probes in the SARS-CoV oligochromatographic device were coupled to colloidal gold particles as described above. These oligonucleotides are the following: one specific for the SARS-COV target gene (5' CCCTCTGCTGGCGAAAAGTG 3'), and one specific for the internal control, the same as for the *T. gondii* internal control (5' AGGGTCTACTACTGGGTTACCTG 3').

The Oligochromatographic Device oligochromatographic device that was used in the present is very similar to the device used for the *T. gondii* amplicon detection. The control side is identical to that of the *T. gondii* oligochromatographic stick. On the test side, the nitrocellulose membrane was sensitized with neutralite avidine. The SARS-CoV specific oligonucleotidic probe conjugate is impregnated in the polyester membrane (MDI) of the application region of this test side.

The SARS-CoV RT-PCR Internal Control

The internal control is designed as to show if a negative SARS-CoV test result is a true negative, i.e. that the negative result is not due to a reverse transcription or an amplification inhibitory substance possibly present in the tested sample. This internal control is a RNA template that is added to the reaction mix before the RT-PCR, and should be retro-transcribed and amplified at least in the absence of SARS-CoV target gene, unless an inhibitory substance is present in the sample. The internal control template is a RNA template. This RNA was designed such as that the internal control amplicon will match the following criteria:

- same length as the target amplicon
- same G/C content as the target amplicon
- retro-transcribed and amplified with the same oligonucleotidic primers as the target amplicon
- in the internal part of this internal control template, the sequence of the SARS-CoV target gene probe is replaced by the sequence of the internal control probe. In that way, the SARS-COV specific probe does not hybridize to the internal control amplicon, and the internal control probe does not hybridize to the SARS-CoV target gene amplicon. The internal control template RNA was produced by in vitro transcription using a T7 RNA polymerase as described by the manufacturer (Epicentre).

The template used for this in vitro transcription was a double-stranded DNA which sequence comprises a promoter sequence for the T7 RNA polymerase followed by the sequence of the internal control RNA template to be produced. The sequence of this double-stranded DNA was the following (sequence corresponding to the RNA transcript is underlined):

5' TAATACGACTCACTATAGGGAGGCACCCGCGAAGAAGCTATTCTTTA
GGGTCTACTGGGTTACCTGCCGGATGTAGAGGGCTGTCATGCAA 3'.

The quantity of the SARS-CoV internal control template RNA to be added to the RT-PCR mix must allow retro-transcription and amplification of this internal control in all cases in the absence of sample.

DNA Extraction

Extraction of RNA from samples suspected to contain SARS-CoV can be realized by any method, either commercially available or described in the scientific literature. Extracted RNA is used directly after extraction or kept at −80° C. until use.

Amplification of Target RNA

SARS-COV target gene amplification was performed by RT-PCR with a biotin-labelled reverse primer (sequence: 5' TTGCATGACAGCCCTCTACATC 3') and a non-labelled forward primer (sequence: 5' CACCCGCGAAGAAGCTATTC 3'. The reverse primer acts both as primer for the target-specific reverse transcription and for the amplification whereas the forward primer acts only for the amplification reaction. RT-PCR was carried out with the "One-Step RT-PCR kit" from Qiagen essentially according to the manufacturer's instructions.

Briefly, a 50 μl RT-PCR reaction contains the following components:

- Qiagen One-Step RT-PCR buffer, 5× concentrated: 10 μl
- dNTP mix 10 mM from the Qiagen kit: 2 μl
- Oligo forward: 0.15 μM final concentration
- Oligo reverse: 0.6 μM final concentration
- Enzyme mix from the Qiagen kit: 2 μl
- Internal control RNA template: dilution from the in vitro transcribed RNA to be determined for each batch of RNA
- Sample (extracted RNA): 1 μl to 5 μl
- Molecular biology-grade water (RNAse and DNase-free): to a final volume of 50 μl The reaction mix is kept on ice until beginning of the RT-PCR. Thermal cycler is preheated to 50° C. before placing the RT-PCR tubes in it.

RT-PCR is performed with the following thermic cycles:

- 30 minutes at 50° C.
- 15 minutes at 94° C.
- 45 cycles (20 seconds at 94° C., 20 seconds at 55° C., 30 seconds at 72° C.)
- 1 minutes at 72° C.
- 30 seconds at 94° C.

Amplified products are the stored at 4° C. until further use.

SARS-CoV Detection

The detection is performed identically as for *T. gondii* amplified products detection.

Double-sided nitrocellulose laminates are also useful for immunochromatographic purposes, for detection of numerous different analytes in so-called multiplex detection mode.

The invention claimed is:

1. A sheet-like chromatographic device comprising:
an application region, and
a detection region,
wherein the detection region comprises at least one capture reagent, the capture reagent effective to bind to a hapten or peptide of a hapten/peptide conjugated analyte oligonucleotide which comprises a hapten or peptide bonded to an analyte oligonucleotide chain, and wherein the application region comprises at least one labeled probe conjugate effective to be hybridized to the analyte oligonucleotide and which labeled probe conjugate is effective to allow the detection of the analyte oligonucleotide, the labeled probe conjugate comprising an oligonucleotide conjugated to a visible label, the visible label being selected from the group consisting of conjugated metallic colloids, conjugated latex particles, and microparticles having a specific color.

2. The sheet-like chromatographic device according to claim 1, wherein the analyte oligonucleotide is identical to one of primers used for the molecular amplification of the analyte.

3. The sheet-like chromatographic device according to claim 1, wherein the chromatographic device is made of double-sided nitrocellulose laminates which further comprises a test side and a control side, the test side containing the capture reagent effective to bind to the hapten or peptide and the control side containing the capture reagent to effect an internal amplification control.

4. The sheet-like chromatographic device according to claim 3, wherein the control side contains a chromatographic control comprising a control oligonucleotide sequence complementary to a control probe conjugate.

5. The sheet-like chromatographic device according to claim 1, wherein the reagent comprises molecules able to bind the hapten or peptide, the molecules selected from the group consisting of polyclonal antibody, monoclonal antibody, and hypervariable antibody fragment.

6. The sheet-like chromatographic device according to claim 1, wherein the chromatographic device is selected from the group consisting of a dipstick and a lateral flow device.

7. The sheet-like chromatographic device according to claim 1, wherein the chromatographic device comprises polymeric substances laminated on a rigid solid support.

8. The sheet-like chromatographic device according to claim 7, wherein the rigid solid support is a polymer support.

9. The sheet-like chromatographic device according to claim 1, wherein the detection region comprises a control region.

10. The sheet-like chromatographic device according to claim 1, further comprising an absorbent region.

11. The sheet-like chromatographic device according to claim 1, wherein the application region comprises a conjugate pad.

12. The sheet-like chromatographic device according to claim 11, wherein the application region and the conjugate pad are made of the same material.

13. A method for detecting and/or quantifying at least one analyte in a biological sample by detecting the presence or absence of an analyte oligonucleotide chain obtained from a molecular amplification of the analyte, wherein the analyte oligonucleotide chain is put in contact with the sheet-like chromatographic device according to claim 1.

14. The sheet-like chromatographic device according to claim 10, wherein the application region comprises a membrane made of glass fibers with a conjugate pad made of polyester, wherein the detection region comprises a membrane selected from the group consisting of nitrocellulose, nylon and polyether sulfone membrane, and wherein the absorbent region comprises a membrane made of cellulose.

15. The sheet-like chromatographic device according to claim 1 wherein the capture reagent comprises an antibody.

16. A sheet-like chromatographic device comprising:
an application region, and
a detection region,
wherein the detection region comprises at least one capture reagent which is effective to bind to a hapten or peptide, the hapten or peptide bonded to an analyte nucleotide sequence chain which is specific to a target polynucleotide, and
wherein the application region comprises at least one visible probe conjugate comprising an oligonucleotide conjugated to a visible label, the oligonucleotide having a nucleotide sequence effective for hybridizing to the analyte nucleotide chain bonded to the hapten or peptide to form a hybridized combination of the visible probe conjugate and the analyte nucleotide chain, the hapten or peptide on the chain of the analyte nucleotide effective for reacting with the capture reagent and bonding the hybridized combination to the capture reagent which allows the detection of the analyte nucleotide chain conjugated to the hapten or peptide by generating a signal with the visible label, and wherein the visible label is selected from the group consisting of conjugated metallic colloids, conjugated latex particles, and microparticles having a specific color.

17. The sheet-like chromatographic device according to claim 16, wherein the chromatographic device is made of double-sided nitrocellulose laminates which further comprises a test side and a control side, the test side containing reagents for the detection of the target polynucleotide and the control side containing reagents for the detection of an internal amplification control.

18. The sheet-like chromatographic device according to claim 16, wherein the capture reagent comprises molecules able to bind the hapten or peptide, the molecules selected from the group consisting of polyclonal antibody, monoclonal antibody, and hypervariable antibody.

19. A method for detecting and/or quantifying at least one analyte in a biological sample by detecting the presence or absence of an analyte nucleotide chain obtained from a molecular amplification of an analyte, wherein the analyte nucleotide chain is put in contact with the sheet-like chromatographic device according to claim 16.

20. The sheet-like chromatographic device according to claim 16 wherein the capture reagent comprises an antibody.

21. A sheet-like chromatographic device comprising:
an application region which comprises at least one labeled probe conjugate effective to hybridize to a hapten/peptide analyte conjugate, the hapten/peptide analyte conjugate including an analyte nucleotide chain bonded to a hapten or peptide, the labeled probe conjugate comprising an oligonucleotide conjugated to a visible label, the visible label being selected from the group consisting of conjugated metallic colloids, conjugated latex particles, and microparticles having a specific color effective to allow the detection of the analyte nucleotide chain; and
a detection region comprising at least one capture reagent, the capture reagent bound to the hapten or peptide on the analyte nucleotide chain of the hapten/peptide analyte conjugate, and the analyte nucleotide chain of the hapten/peptide analyte conjugate detectable in the detection region by the visible label of the labeled probe conjugate bonded to the hapten/peptide analyte conjugate.

22. The sheet-like chromatographic device according to claim 21, wherein the analyte oligonucleotide chain is identical to one of primers used for the molecular amplification of the analyte.

23. The sheet-like chromatographic device according to claim 21, wherein the chromatographic device is made of double-sided nitrocellulose laminates which further comprises a test side and a control side, the test side containing a capture reagent which bonds to the hapten or peptide and the control side containing capture reagent which bonds to the hapten or peptide to effect internal amplification control.

24. The sheet-like chromatographic device according to claim 23, wherein the control side contains a chromatographic control comprising a control oligonucleotide sequence complementary to a control probe conjugate.

25. The sheet-like chromatographic device according to claim 21, wherein the capture reagent includes molecules selected from the group consisting of polyclonal antibody, monoclonal antibody, and hypervariable antibody fragment.

26. The sheet-like chromatographic device according to claim 21, wherein the application region comprises a membrane made of glass fibers with a conjugate pad made of polyester, wherein the detection region comprises a membrane selected from the group consisting of nitrocellulose, nylon and polyether sulfone membrane, and wherein the absorbent region comprises a membrane made of cellulose.

27. The sheet-like chromatographic device according to claim 26, wherein the application region and the conjugate pad are made of the same material.

28. A method for detecting at least one analyte in a sample with a sheet-like chromatographic device having an application region and a detection region, the method comprising:
contacting the application region of the sheet-like chromatographic device with a sample comprising a hapten/peptide analyte conjugate, the hapten/peptide analyte conjugate comprising an analyte nucleotide chain bonded to a hapten or peptide, and the application region comprising at least one labeled probe conjugate comprising an oligonucleotide conjugated to a visible label, the visible label being selected from the group consisting of conjugated metallic colloids, conjugated latex particles, and microparticles having a specific color effective to allow the detection of the analyte nucleotide chain;
forming a complex between the hapten/peptide analyte conjugate and the labeled probe conjugate;
capturing the complex at the detection region, the detection region comprising a capture reagent and the capturing occurring by interaction of the hapten or peptide of the hapten/peptide analyte conjugate with the capture reagent; and
detecting the hapten/peptide analyte conjugate in the detection region by the visible label of the labeled probe conjugate complexed with the hapten/peptide analyte conjugate.

29. The method according to claim 28, wherein the analyte oligonucleotide chain is identical to one of primers used for the molecular amplification of the analyte.

30. The method according to claim 28, wherein the chromatographic device is made of double-sided nitrocellulose laminates which further comprises a test side and a control side, the test side containing the capture reagent which bonds to the hapten or peptide and the control side containing the capture reagent which bonds to the hapten or peptide to effect internal amplification control.

31. The method according to claim 30, wherein the control side contains a chromatographic control comprising a control oligonucleotide sequence complementary to a control probe conjugate.

32. The method according to claim 28, wherein the capture reagent includes an agent selected from the group consisting of polyclonal antibody, monoclonal antibody, and hypervariable antibody fragment.

33. The method according to claim 28, wherein the application region comprises a membrane made of glass fibers with a conjugate pad made of polyester, wherein the detection region comprises a membrane selected from the group consisting of nitrocellulose, nylon and polyether sulfone membrane, and wherein the absorbent region comprises a membrane made of cellulose.

34. The sheet-like chromatographic device according to claim 28, wherein the application region and the conjugate pad are made of the same material.

* * * * *